United States Patent
Blumhagen et al.

(10) Patent No.: US 9,445,722 B2
(45) Date of Patent: Sep. 20, 2016

(54) METHOD FOR PERFORMING COMBINED MAGNETIC RESONANCE/POSITRON EMISSION TOMOGRAPHY

(71) Applicants: Jan Ole Blumhagen, Erlangen (DE); Matthias Fenchel, Erlangen (DE); Ralf Ladebeck, Erlangen (DE)

(72) Inventors: Jan Ole Blumhagen, Erlangen (DE); Matthias Fenchel, Erlangen (DE); Ralf Ladebeck, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 297 days.

(21) Appl. No.: 13/792,502

(22) Filed: Mar. 11, 2013

(65) Prior Publication Data

US 2013/0237806 A1 Sep. 12, 2013

(30) Foreign Application Priority Data

Mar. 12, 2012 (DE) .................. 10 2012 203 782

(51) Int. Cl.
*A61B 5/055* (2006.01)
*A61B 5/00* (2006.01)
(Continued)

(52) U.S. Cl.
CPC ............ *A61B 5/0035* (2013.01); *A61B 5/055* (2013.01); *A61B 6/037* (2013.01); *A61B 6/4417* (2013.01); *A61B 6/5247* (2013.01);
(Continued)

(58) Field of Classification Search
CPC .... A61B 5/0035; A61B 5/055; A61B 6/037; A61B 6/4417; A61B 6/5247; G01R 33/481; G01R 33/56563; G01R 33/56572
See application file for complete search history.

(56) References Cited

U.S. PATENT DOCUMENTS

| 5,924,987 A * | 7/1999 | Meaney et al. ............... 600/420 |
| 6,529,762 B1 | 3/2003 | Ladebeck |

(Continued)

FOREIGN PATENT DOCUMENTS

| CN | 101390754 A | 3/2009 |
| CN | 101680938 A | 3/2010 |

(Continued)

OTHER PUBLICATIONS

Bakker CJ et al.: "Analysis of machine-dependent and object-induced geometric distortion in 2DFT MR imaging" in Magn Reson Imaging, 1992, vol. 10(4), pp. 597-608; Others; 1992.

(Continued)

*Primary Examiner* — Ruth S Smith
(74) *Attorney, Agent, or Firm* — Harness, Dickey & Pierce, P.L.C.

(57) ABSTRACT

A method is disclosed for performing a combined magnetic resonance/positron emission tomography scan of an examination object in an MR/PET system. An embodiment of the method entails acquiring first magnetic resonance data using a first readout gradient field. The first readout gradient field is chosen such that, at a location of the field of view of the magnetic resonance system, a distortion caused by a non-linearity of the first readout gradient field and a distortion caused by a $B_0$ field inhomogeneity substantially cancel each other out. First magnetic resonance images for planning the combined magnetic resonance/positron emission tomography session and determining an attenuation correction map for a positron emission tomography scan are determined on the basis of the first magnetic resonance data. Positron emission data and second magnetic resonance data are acquired using a second readout gradient field.

11 Claims, 4 Drawing Sheets

(51) Int. Cl.
*A61B 6/03* (2006.01)
*G01R 33/48* (2006.01)
*G01R 33/565* (2006.01)
*A61B 6/00* (2006.01)

(52) U.S. Cl.
CPC ..... *G01R 33/481* (2013.01); *G01R 33/56563* (2013.01); *G01R 33/56572* (2013.01)

(56) References Cited

U.S. PATENT DOCUMENTS

| | | | |
|---|---|---|---|
| 8,565,505 B2* | 10/2013 | Bergmans | G01R 33/54 378/4 |
| 2009/0105583 A1* | 4/2009 | Martin et al. | 600/422 |
| 2009/0177078 A1* | 7/2009 | Takizawa et al. | 600/415 |
| 2010/0189328 A1* | 7/2010 | Boernert et al. | 382/131 |
| 2010/0312091 A1* | 12/2010 | Krueger | G01R 33/285 600/410 |
| 2011/0074407 A1 | 3/2011 | Ladebeck | |
| 2011/0187364 A1 | 8/2011 | Blumhagen et al. | |
| 2012/0056621 A1 | 3/2012 | Blumhagen et al. | |

FOREIGN PATENT DOCUMENTS

| | | |
|---|---|---|
| DE | 19943404 A1 | 4/2001 |
| DE | 102009043449 A1 | 4/2011 |
| DE | 102010044520 A1 | 3/2012 |
| EP | 0344518 A1 | 12/1989 |

OTHER PUBLICATIONS

J. O. Blumhagen et al., "MR-based Field-of-View Extension: Compensation of Field Imperfections", In Proc. Intl. Soc. Mag. Reson. Med. 19, 2011, p. 2693; Others; 2011.

Axel Martinez-Möller et al: Tissue classification as a potential approach for attenuation correction in whole-body PET/MRI: evaluation with PET/CT data; J Nucl Med. 2009;50:520-526; Others; 2009.

Nuyts J et al: "Completion of a truncated attenuation image from the attenuated PET emission data", IEEE Nucl Sci Symp Conf Record 2010.; Others; 2010.

German Office Action for German Application 10 2012 203 782.9 dated Nov. 7, 2012.

Chinese Office Action and English translation thereof dated Jul. 3, 2015.

* cited by examiner

METHOD FOR PERFORMING COMBINED MAGNETIC RESONANCE/POSITRON EMISSION TOMOGRAPHY

PRIORITY STATEMENT

The present application hereby claims priority under 35 U.S.C. §119 to German patent application number DE 10 2012 203 782.9 filed Mar. 12, 2012, the entire contents of which are hereby incorporated herein by reference.

FIELD

At least one embodiment of the present invention generally relates to a method for performing a combined magnetic resonance/positron emission tomography scan of an examination object in a hybrid magnetic resonance/positron emission tomography system, called an MR/PET system for short. At least one embodiment of the present invention also generally relates to a magnetic resonance/positron emission tomography system employing the method.

BACKGROUND

Human attenuation correction in a positron emission tomography session can be carried out on the basis of magnetic resonance data. In magnetic resonance systems the volume that can be used for acquired magnetic resonance tomography images within the tomography apparatus is limited in all three spatial directions due to physical and technical constraints, such as a limited homogeneity of the magnetic field, for example, and a nonlinearity of the gradient field. For this reason a usable acquisition volume for magnetic resonance tomography images, what is referred to as a usable field of view (FoV), is restricted to a volume in which the aforementioned physical properties lie within predefined tolerance ranges and consequently true-to-the-original imaging of the object to be examined is possible using conventional magnetic resonance measurement sequences.

Strong distortions of the measurement object occur outside of this usable field of view and true-to-the-original imaging cannot be guaranteed using conventional measurement sequences. What is meant by distortion in this context is that a signal value of the examination object at a predefined location appears at a different location in the image of the examination object determined from the acquired magnetic resonance data.

The coordinates of the predefined location are also referred to as the actual position and the coordinates in the image determined from the acquired magnetic resonance data are also referred to as the distorted position. Distortions which cannot be compensated by subsequent rectification of the image of the examination object can occur in particular outside the usable field of view, because for example a plurality of adjacent actual positions can be mapped to one or more distorted positions that are located close to one another. The thus delimited field of view is considerably smaller, in particular in the x- and y-direction, i.e. perpendicularly to a longitudinal axis of a tunnel of the magnetic resonance system, than the volume delimited by the tunnel of the magnetic resonance system. In conventional magnetic resonance systems the tunnel has for example a diameter in the 60-70 cm range, whereas the diameter of the normally usable field of view in which the aforementioned physical conditions lie within the tolerance ranges is approximately 10 cm smaller, in other words in a range of 50-60 cm.

In an MR/PET system in which the human attenuation correction for the positron emission tomography session is to be carried out on the basis of the magnetic resonance data, an image of the examination object that is true to the original and precise in terms of location is also necessary in a peripheral region between the above-described normally usable field of view and the inner wall of the tunnel, since for example the arms of a patient may also be arranged in said peripheral region, the position of the arms being required for determining the attenuation correction for the acquisition of the PET image. Even small distortions of the underlying magnetic resonance data can greatly affect the attenuation correction factors, because the attenuation correction factors are an exponential function of the attenuation p, the correction of the PET scattering, called "scatter correction", requires a distortion-free attenuation correction map, and the so-called "scatter scaling" requires a precise specification of the contours of the examination object.

According to the prior art, as known for example from the publication titled "Tissue classification as a potential approach for attenuation correction in whole-body PET/MRI: evaluation with PET/CT data" by Martinez-Möller A, Souvatzoglou M, Delso G, et al., from J Nucl Med. 2009; 50:520-526, an attenuation correction in the torso can be determined by way of a 2-point DIXON method and a segmentation into four classes (soft tissue, fat, lung, background).

It is also known for example from the publication titled "Completion of a Truncated Attenuation Image from the Attenuated PET Emission Data" by Nuyts J, Michel C, Fenchel M, Bal G, Watson G, from IEEE Nucl Sci Symp Conf Record 2010, that missing portions in an attenuation correction map can be estimated retrospectively from the PET data by way of a maximum-likelihood a-posteriori algorithm. However, a disadvantageous aspect with this method is the great amount of time required for performing the calculation as well as a limitation to specific PET tracers having a sufficiently high uptake in the arms and skin. Furthermore, there can be difficulties with certain PET applications (for example dynamics), since the profile of the PET tracer uptake can change over time. What's more, the accuracy of the position determination is dependent on the quality of the PET statistics, since the actual position of the arms for example is not determined by MR-based measurement, but is calculated from the PET projection data.

Furthermore, a method for determining a position of a subregion of an examination object in a magnetic resonance system is disclosed by the patent application with the application number DE 10 2010 006 431 A1 of the same inventor. The subregion of the examination object is arranged at the edge of the field of view of the magnetic resonance system. With the method, at least one slice position for a magnetic resonance image in which the B0 field at the edge of the magnetic resonance image fulfills a predetermined homogeneity criterion is determined automatically. Furthermore, a magnetic resonance image including the subregion at the edge of the field of view is acquired in the specific slice position. The location of the subregion of the examination object is determined automatically on the basis of the location of the subregion in the acquired magnetic resonance image. A disadvantageous aspect with this method is the additional time required for the additional magnetic resonance measurement.

SUMMARY

A suitable true-to-the-original imaging of structures of an object is provided in at least one embodiment, that is to be examined in a region outside of the usual field of view, i.e. for example in a peripheral region of a ring tunnel of the magnetic resonance system, within the framework of a magnetic resonance/positron emission tomography session, without the time required for performing the entire magnetic resonance/positron emission tomography session being substantially increased.

At least one embodiment of the invention is directed to a method for performing a combined magnetic resonance/positron emission tomography scan of an examination object in a MR/PET system, a magnetic resonance/positron emission tomography system, a computer program product as, and/or an electronically readable data medium. The dependent claims define preferred and advantageous embodiment variants of the invention.

According to at least one embodiment of the present invention, a method is provided for performing a combined magnetic resonance/positron emission tomography scan of an examination object in a MR/PET system. With the method, first magnetic resonance data are acquired using a first readout gradient field. The first readout gradient field is chosen such that at a predetermined location of the field of view of the magnetic resonance system a distortion caused by a nonlinearity of the first readout gradient field and a distortion caused by a B0 field inhomogeneity substantially cancel each other out. Magnetic resonance images used for planning the combined magnetic resonance/positron emission tomography session are determined on the basis of the first magnetic resonance data.

BRIEF DESCRIPTION OF THE DRAWINGS

The invention is explained below on the basis of preferred embodiment variants and with reference to the drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to at least one embodiment of the present invention, a method is provided for performing a combined magnetic resonance/positron emission tomography scan of an examination object in a MR/PET system. With the method, first magnetic resonance data are acquired using a first readout gradient field. The first readout gradient field is chosen such that at a predetermined location of the field of view of the magnetic resonance system a distortion caused by a nonlinearity of the first readout gradient field and a distortion caused by a B0 field inhomogeneity substantially cancel each other out. Magnetic resonance images used for planning the combined magnetic resonance/positron emission tomography session are determined on the basis of the first magnetic resonance data.

Also determined on the basis of the first magnetic resonance images is an attenuation correction map for a positron emission tomography scan. Positron emission data and second magnetic resonance data are acquired in a for example simultaneous MR/PET measurement, for example in succession for each table position of an examination table of the MR/PET system or during a measurement with continuously moving table. The second magnetic resonance data are acquired using a second readout gradient field. Preferably the first magnetic resonance data are acquired first and the acquisition of the positron emission data and the second magnetic resonance data is performed on the basis of the planning produced therefrom. The first magnetic resonance data accordingly serve both as planning data for planning the MR/PET measurement and for determining an attenuation correction map for the positron emission tomography session. Since magnetic resonance images for a so-called localizer sequence are usually acquired and generated anyway in magnetic resonance/positron emission tomography sessions in order to obtain an approximate structure of the anatomy of the examination object as a basis for the further planning, the above-described method according to at least one embodiment of the invention requires no or only a few additional MR measurements, with the result that the time required for performing the entire combined magnetic resonance/positron emission tomography session is not significantly increased.

The predetermined location at which a distortion caused by the nonlinearity of the first readout gradient field and the distortion caused by the B0 field inhomogeneity substantially cancel each other out can include a location in a peripheral region of the field of view of the magnetic resonance system. The gradient field can be for example a readout gradient field or a slice selection gradient field. Since the nonlinearity of the gradient field is dependent on the gradient field strength and the B0 field inhomogeneities are not dependent on the gradient field strength, the gradient field can be set at least for a predetermined location of the field of view or a predetermined region of the field of view in such a way that the nonlinearity of the gradient field and the B0 field inhomogeneity at this location or in this region cancel each other out. A distortion for this predetermined location or for the predetermined region can be avoided as a result.

Accordingly, a usable image of the examination object can be determined for this location or region even if the location or the region is situated outside of a normally usable region of the field of view of the magnetic resonance system, for example in an inner casing area along an inner surface of a tunnel-shaped bore of the magnetic resonance system through which the examination object is guided in the magnetic resonance system. The inner casing area can have for example an inner casing thickness of approximately 5 cm, i.e. the inner casing area relates to an area in which generally, due to physical and/or technical limitations of the magnetic field homogeneity and the linearity of the gradient field, it is not possible to generate magnetic resonance images that are free of distortion. As mentioned hereintofore, however, a subregion of the examination object, for example an arm of a patient, may be arranged precisely in said inner casing area. Low distortion is achieved in the peripheral region owing to the suitably chosen first readout gradient field, with the result that an arrangement of the examination object in the peripheral region, for example of the arm of the patient, can be reliably determined. Preferably the magnetic resonance data are acquired in a transverse plane with respect to the examination object.

Owing to the low degree of distortion the position of the examination object, in particular for example an arm, can be reliably determined from the magnetic resonance image of the examination object and consequently an accurate attenuation correction map can be generated for the positron emission tomography session. In positron emission tomography, taking account of the attenuation of the received radiation (photons) due to the structure or anatomy of the examination object in the beam direction is crucially important. Because the position of the subregion of the examination object at the edge of the field of view of the magnetic resonance system can also be determined, an overall determination of the position and structure of the examination object or patient in the magnetic resonance system is possible, and consequently a precise attenuation correction for a positron emission tomography measurement can be achieved. Since the attenuation correction is in this case based solely on information from the magnetic resonance imaging, a positron emission tomography session can also be performed with less strongly concentrated PET tracers. Following the acquisition the positron emission data can be corrected by means of the attenuation correction map.

According to an embodiment variant the second readout gradient field is independent of the first readout gradient field. Furthermore, the first magnetic resonance data can be acquired at a first resolution and the second magnetic resonance data can be acquired at a second resolution. The second resolution can be higher than the first resolution. To put it another way, the acquisition of the second magnetic resonance data is independent of the acquisition of the first magnetic resonance data. The first magnetic resonance data are, as described hereintofore, acquired in such a way that distortion-free magnetic resonance images can be generated at a predetermined location of the field of view, in particular in a peripheral region of the field of view. Furthermore, the first magnetic resonance data can be acquired in respect of slice thickness, slice spacing or image quality in such a way that they supply magnetic resonance images that are suitable for planning the combined magnetic resonance/positron emission tomography session. The second readout gradient field can in contrast be chosen such that optimal or suitable magnetic resonance images can be acquired for a diagnostic magnetic resonance/positron emission tomography session for example. Equally, the second resolution can be suitably chosen accordingly, whereas the first resolution is simply chosen high enough to supply sufficient information for the localizer sequence and the attenuation correction map. As a result the combined magnetic resonance/positron emission tomography session can be performed quickly and with high quality.

According to an embodiment variant the acquisition of the first magnetic resonance data includes a continuous moving of the examination object through the MR/PET system. Given a suitably chosen first readout gradient field, magnetic resonance data can be acquired free of or low in distortion within the normally used field of view of the magnetic resonance system as well as at one or more predetermined locations outside of the normally used field of view, i.e. in the peripheral region of the field of view. Because the examination object is moved continuously through the MR/PET system during the acquisition of the first magnetic resonance data, anatomical data of the examination object can be acquired free of or low in distortion in the peripheral region of the field of view at the predetermined location or region, such that at the end, after the examination object has been moved in its entirety through the MR/PET system, a distortion-free or low-distortion image of the anatomy of the examination object can be obtained.

According to an embodiment variant the first magnetic resonance data are acquired by way of a multi-echo sequence. As described hereintofore, a first readout gradient field is determined in such a way that at the predetermined location of the field of view, for example in the peripheral region of the field of view, a distortion caused by a nonlinearity of the first readout gradient field and a distortion caused by a B0 field inhomogeneity substantially cancel each other out. Furthermore, a further readout gradient field is determined in such a way that at a further predetermined location of the field of view, for example at a further location in the peripheral region of the field of view, a distortion caused by a nonlinearity of the further readout gradient field and a distortion caused by the B0 field inhomogeneity substantially cancel each other out.

In order to perform the multi-echo sequence, first magnetic resonance data of a first spin echo are acquired following a 180° pulse using the first readout gradient field, and following a further 180° pulse further magnetic resonance data of a second spin echo are acquired using the further readout gradient field. The first magnetic resonance images are determined on the basis of the first magnetic resonance data and the further magnetic resonance data for the purpose of planning the combined magnetic resonance/positron emission tomography session and determining the attenuation correction map. The predetermined location and the further predetermined location are different locations and in each case locations in an inner casing area which is delimited on the one hand by a normally usable field of view of the magnetic resonance system and on the other hand by a tunnel-shaped bore of the magnetic resonance system serving to receive the examination object. The two locations can lie for example in a slice of a magnetic resonance image. Preferably the first readout gradient field and the further readout gradient field have the same gradient direction and the predetermined location and the further predetermined location are arranged at substantially opposite ends of the field of view of the magnetic resonance system in the gradient direction.

Alternatively, the further 180° pulse can also be omitted, with the further magnetic resonance data then being acquired in the course of a mixed spin echo/gradient echo sequence using the further readout gradient field. The entire readout sequence can be simplified in this way.

Since the nonlinearity of the gradient field is dependent on the gradient field strength and the B0 field inhomogeneities are not dependent on the gradient field strength, the gradient field can be determined and generated, at least for a predetermined location of the field of view or a predetermined region of the field of view, in particular also in the peripheral region of the field of view between the normally usable field of view and the inside of the tunnel-shaped bore, in such a way that the nonlinearity of the gradient field and the B0 field inhomogeneity at this location or in this region cancel each other out. However, because a separate magnetic resonance data acquisition using the corresponding gradient field is necessary for each such predetermined location, the time required for acquiring magnetic resonance data for a magnetic resonance image increases considerably overall if a plurality of different locations are to be acquired. In order to reduce this measurement time, the multi-echo sequence is performed in which a corresponding readout gradient field which is optimized for a predetermined location is switched following a 180° pulse in each case. By various of said readout gradient fields for different locations or regions being switched following a 180° pulse in each case, magnetic resonance data can be acquired which supply distortion-free information for the different locations. Thus, magnetic resonance data can be acquired in a short time for the purpose of generating magnetic resonance images in which only minor distortions are present.

In the above-described method the first readout gradient field is chosen in such a way that at the predetermined location a distortion caused by the nonlinearity of the first readout gradient field and a distortion caused by the B0 field inhomogeneity substantially cancel each other out. In the ideal case the distortions at the respective location therefore cancel each other out completely. A complete mutual cancelation is not absolutely essential, however, and often is not technically possible. For an advantageously usable distortion correction it is therefore sufficient if the distortion due to the nonlinearity of the readout gradient field and the distortion due to the B0 field inhomogeneity cancel each other out to a great extent at the respective location. This state of affairs is expressed by the wording "substantially cancel each other out". Within the context of this description the formulations used in this connection, namely "cancel each other out" and "substantially cancel each other out", are to be understood in the above-described way.

Also provided according to at least one embodiment of the present invention is a magnetic resonance/positron emission tomography system which comprises a basic field magnet, a gradient field system, a radio-frequency antenna, and a control device for controlling the gradient field system and the radio-frequency antenna, for receiving measurement signals picked up by the radio-frequency antenna, for evaluating the measurement signals, and for generating magnetic resonance images. The system is able to acquire first magnetic resonance data using a first readout gradient field. The first readout gradient field is chosen such that at a predetermined location of the field of view of the magnetic resonance system a distortion caused by a nonlinearity of the first readout gradient field and a distortion caused by a B0 field inhomogeneity substantially cancel each other out. The system is furthermore able to determine first magnetic resonance images on the basis of the first magnetic resonance data for the purpose of planning a combined magnetic resonance/positron emission tomography session. In addition the system is embodied to determine an attenuation correction map for a positron emission tomography scan on the basis of the first magnetic resonance images. Finally the system is embodied to acquire positron emission data and second magnetic resonance data using a second readout gradient field.

The magnetic resonance system can be embodied for performing the above-described method and its embodiment variants and therefore also includes the above-described advantages.

Also provided according to at least one embodiment of the present invention is a computer program product which can be loaded into a memory of a programmable controller of a magnetic resonance/positron emission tomography system. All or various of the above-described embodiment variants of the method according to the invention can be implemented by way of the computer program product when the computer program product runs in the controller. In this case the computer program product may possibly require program segments/modules, for example libraries or help functions, in order to realize the corresponding embodiment variants of the method. To put it another way, it is aimed by way of the claims directed to the computer program product to place under protection in particular a computer program or software by which at least one of the above-described embodiment variants of the method according to the invention can be implemented or which implements the embodiment variant. In this case the software can be a source code, for example C++, which still needs to be compiled or assembled and linked or which only needs to be interpreted, or it can be an executable software code which simply has to be loaded into the corresponding controller in order to execute.

Finally, at least one embodiment of the present invention provides an electronically readable data medium, for example a DVD, a magnetic tape or a USB stick on which electronically readable control information, in particular software, as described hereintofore, is stored. When this control information is read from the data medium and stored in a controller, all of the inventive embodiment variants of the described method can be performed.

Figure 1:
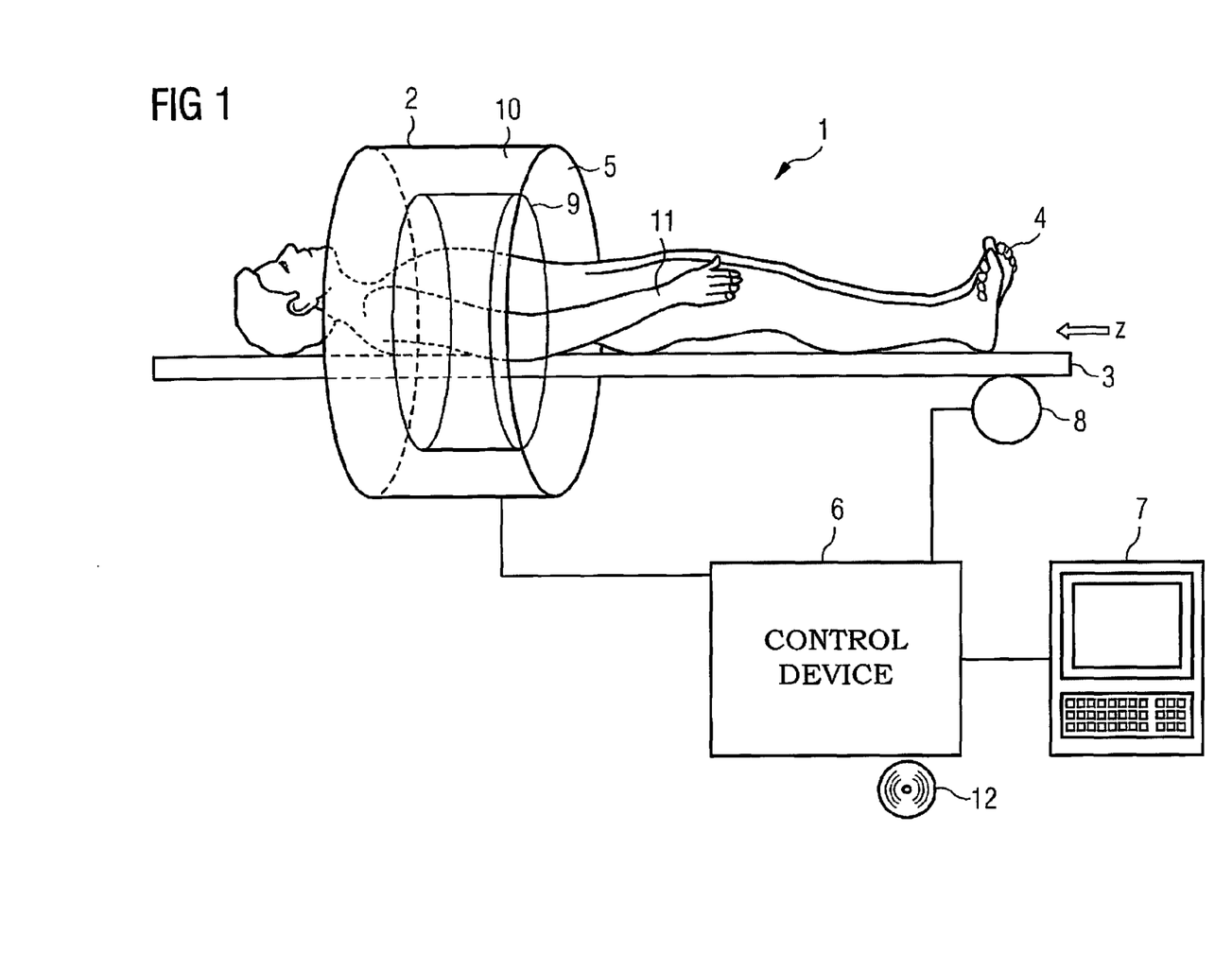
FIG. 1 is a schematic diagram showing a magnetic resonance/positron emission tomography system according to an embodiment variant of the present invention.

FIG. 1 is a schematic diagram showing a magnetic resonance/positron emission tomography system 1. The system 1 comprises the actual tomography apparatus 2, an examination table 3 for a patient 4 which, with the patient 4 positioned on the examination table 3, can be moved through a bore 5 of the tomography apparatus 2, a control device 6, an evaluation device 7, and a drive unit 8. The control device 6 actuates the tomography apparatus 2 and receives signals acquired by the tomography apparatus 2 from the tomography apparatus 2. The tomography apparatus 2 has a basic magnetic field magnet (not shown) for generating a basic magnetic field B0, and a gradient field system (not shown) for generating gradient fields. In addition the tomography apparatus 2 comprises one or more radio-frequency antennas for generating radio-frequency signals and for receiving measurement signals which are used by the control device 6 and the evaluation device 7 for generating magnetic resonance images. The control device 6 actuates the drive unit 8 in order to move the examination table 3 together with the patient 4 in a direction Z through the bore 5 of the tomography apparatus. The control device 6 and the evaluation device 7 can be for example a computer system having a screen, a keyboard and a data medium 12 on which is stored electronically readable control information which is embodied in such a way that it performs the method described below when the data medium is used in the evaluation device 7 and the control device 6.

The magnetic resonance/positron emission tomography system 1 enables magnetic resonance tomography images to be generated inside a volume which is delimited by the bore 5 in the interior of the tomography apparatus 2. Due to physical and technical inadequacies, for example a magnetic field inhomogeneity of the basic magnetic field B0 extending in the Z direction and a nonlinearity of the gradient fields, the volume of the system 1 that can actually be used for the magnetic resonance images is limited to a volume 9 which extends spherically in the interior of the bore 5. In FIG. 1 it is shown that in particular an inner casing area or peripheral region 10 which is located between the usable volume 9 and an inner wall of the tomography apparatus 2 cannot be used, or can be used only to a limited extent, due to the above-described physical and technical inadequacies. In conjunction with a positron emission tomography scan it is however desirable for the magnetic resonance system to be used for determining the position and anatomical structure of the patient 4. At the same time, however, it is necessary to determine the entire anatomical structure of the patient 4, i.e. in particular the anatomical structure of the patient 4 in the inner casing area 10 is also required, which is to say also an arrangement of for example the arms 11 of the patient 4 inside the inner casing area 10. From the acquired anatomical structure of the patient 4 it is then possible to determine a human attenuation correction, referred to as an attenuation correction map, which is of critical importance for the evaluation of the positron emission tomography scan.

Figure 3:
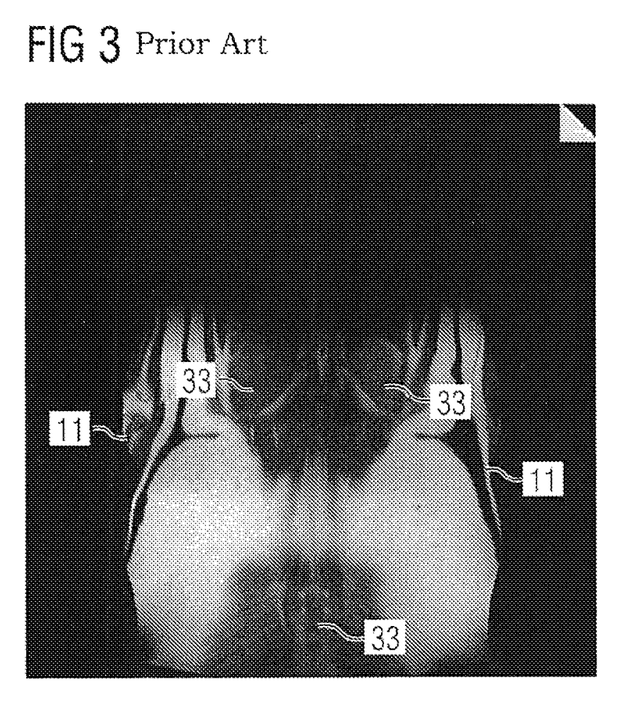
FIG. 3 shows a magnetic resonance image acquired according to the prior art.

FIG. 3 shows a magnetic resonance image acquired according to the prior art, as typically generated during a so-called localizer sequence in order to produce an approximate structure of the anatomy of the patient 4 for the purpose of further planning of the magnetic resonance/positron emission tomography session. Although organs and structures 33 of the patient are very clearly recognizable in the magnetic resonance image for the further planning, the arms 11 are represented seriously distorted because they are located in the inner casing area or peripheral region 10. For this reason no suitable attenuation correction map for a subsequent positron emission tomography scan can be generated on the basis of the thus acquired magnetic resonance images.

As described hereinofore, the usable measurement volume 9 or field of view (FoV) of the magnetic resonance system 1 is limited on the hardware side due to the B0 field homogeneity and the linearity of the gradient field. Measurements outside of the measurement volume 9, in other words in the peripheral region 10 in which the B0 field has inhomogeneities and the gradient field has nonlinearities, lead to severe distortions, i.e. regions of the examination object which are arranged outside of the measurement volume 9 do not appear in the magnetic resonance image at the point at which they are located in reality, but at a position offset thereto, as FIG. 3 shows.

In a magnetic resonance tomography apparatus having for example a tube diameter of 60 cm, the usable measurement volume typically has a diameter of for example 50 cm, i.e. in the peripheral region 10 along the inner circumference of the tomography apparatus 2 the distortion occurs in a range of approx. 5 cm. As a result of the distortion the position of the patient's arms are reproduced incorrectly in the magnetic resonance image. The distortions occurring in this peripheral region are dependent on the field deviation dBg or dB0 relative to the nominal value and on the gradient field strength G. This correlation is known from Bakker C J, et al., Analysis of machine-dependent and object-induced geometric distortion in 2DFT MR imaging, Magn Reson Imaging, 1992, 10(4): 597-608.

The following equations describe by way of example a 2-dimensional magnetic resonance data acquisition with slice selection in the z-direction, phase encoding in the y-direction, and frequency encoding in the x-direction. The phase encoding direction, the frequency encoding direction and the slice selection direction are freely selectable and simply adjust the axis position to the equations.

$$z_1 = z + dB_{gz}(x,y,z)/G_z + dB_0(x,y,z)/G_z \quad (1)$$

$$x_1 = x + dB_{gx}(x,y,z)/G_x + dB_0(x,y,z)/G_x \quad (2)$$

$$y_1 = y + dB_{gy}(x,y,z)/G_y \quad (3)$$

The coordinates (x, y, z) denote the actual positions and the coordinates $(x_1, y_1, z_1)$ the distorted positions.

Distortions due to the gradient field can be both positive and negative in the peripheral region 10, dependent on location, and have different values. Equally, distortions due to the B0 field can be both positive and negative in the peripheral region 10, dependent on location, and have different values.

The distortion generally extends continuously, i.e. the distortion increases in the regions away from the isocenter toward the outside.

Since the nonlinearities dBg of the gradient field scale with the gradient field strength, the distortion can be reduced or compensated in a targeted manner for a specific region or location, as will be shown hereinbelow. The following applies:

$$dB_{gx} = c(x,y,z) \cdot G_x, \quad (4)$$

where c(x, y, z) denotes the relative gradient error at the point x, y, z and $G_x$ represents the gradient field strength. However, the $B_0$ field inhomogeneities are independent of the gradient strength constant. The term $dB_{gx}/G_x$ is therefore constant and independent of the gradient field strength. The term $dB_0/G_x$, on the other hand, is variable with the gradient field strength.

According to an embodiment of the present invention, therefore, the magnetic fields are superimposed in such a way that the nonlinearity of the gradient field and the B0 field inhomogeneity destructively overlay each other at a predetermined location or in a predetermined region. This will be described hereinbelow by way of example for a readout gradient in the x-direction with a slice selection in the z-direction. The required destructive overlaying of the magnetic fields is successful when an optimal gradient strength Gx_opt exists for which the distortion at the predetermined location or within the predetermined region is zero. With a distortion of zero in the x-direction, the following applies:

$$x_1 = x$$

From this it follows that:

$$G_{x\_opt} = -dB_0(x,y,z)/c(x,y,z) \quad (5)$$

If the gradient field strength Gx is chosen as described in equation (5), a significantly enlarged usable field of view is produced for the predetermined position or the predetermined region, i.e. the distortion decreases dramatically in this region.

Figure 4:
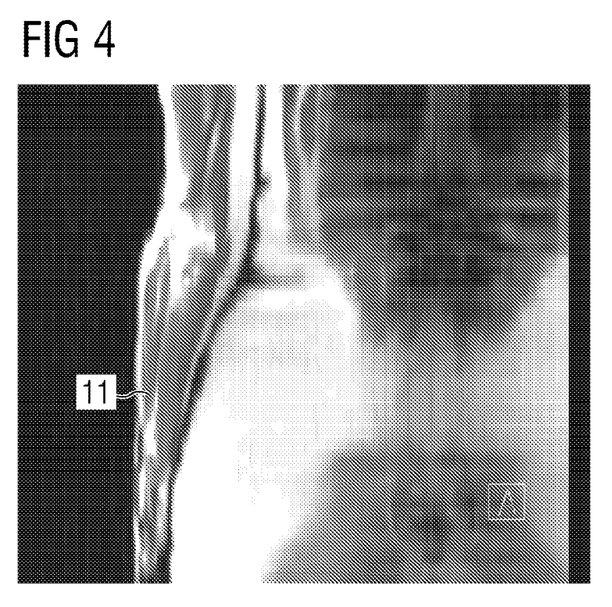
FIGS. 4 and 5 show magnetic resonance images determined according to an embodiment variant of the present invention.
Figure 5:
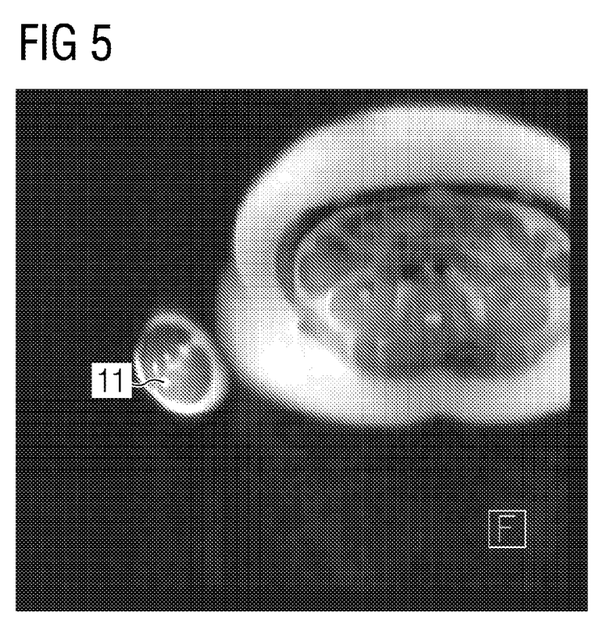

FIGS. 4 and 5 show magnetic resonance images which, as described hereintofore, were acquired by means of a B0 field and gradient fields which were optimized for a distortion-free or low-distortion acquisition in a region in which the patient's arms are usually located. The magnetic resonance images of FIGS. 4 and 5 clearly show that an anatomical structure of the arms 11 now has only very minor distortions and therefore they are suitable for generating an attenuation correction map for a subsequent positron emission tomography scan.

Figure 2:
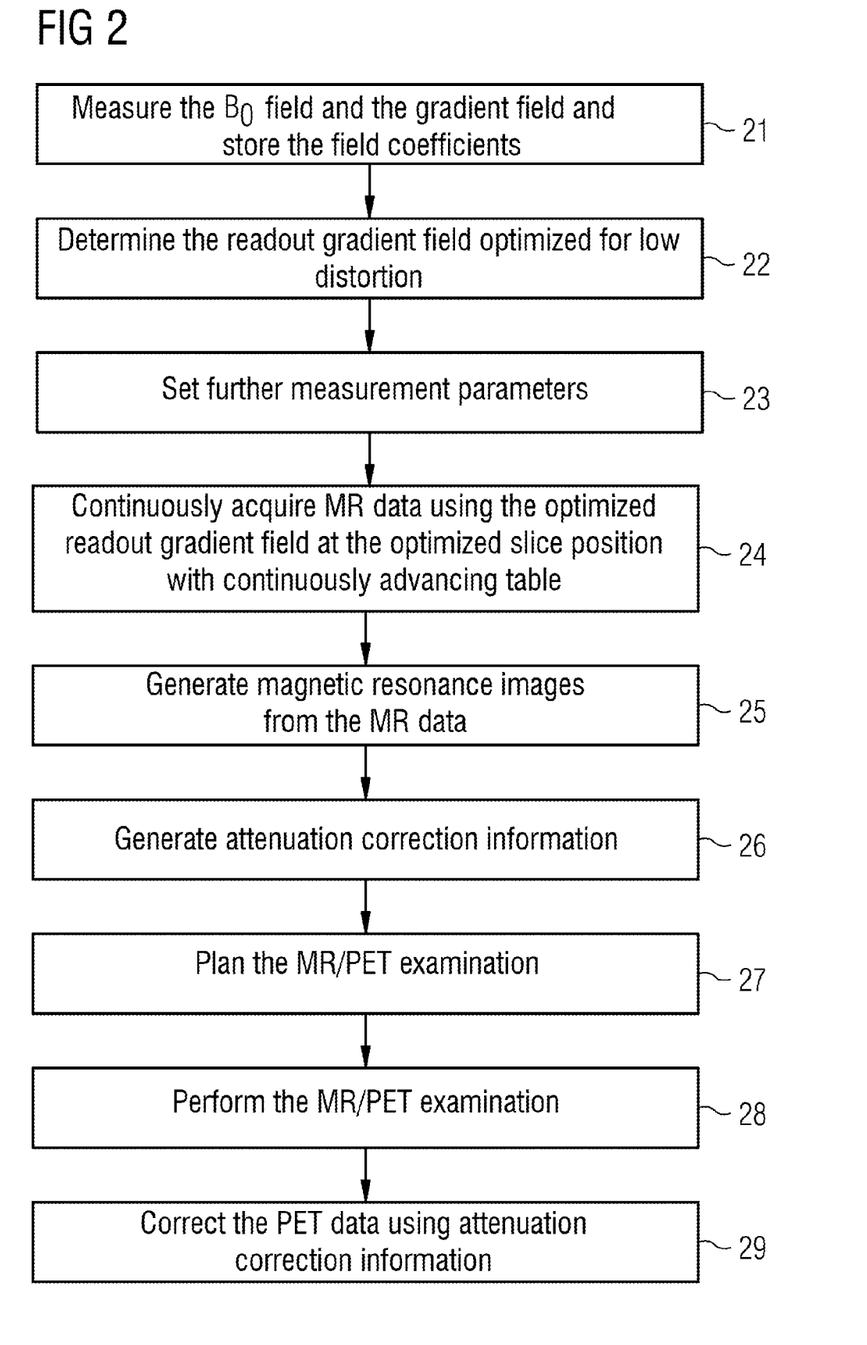
FIG. 2 shows a flowchart comprising method steps according to an embodiment variant of the present invention.

The entire workflow sequence of a combined magnetic resonance/positron emission tomography session is described below with reference to FIG. 2. In step 21, the B0 field and the gradient field within the tomography apparatus 2 are measured and corresponding field coefficients stored. This operation is necessary for example only once at the time of a startup of the system 1. In step 22, a readout gradient field optimized for a predefined position is determined. The readout gradient field is optimized in combination with the B0 field such that only minor or no distortions occur in the predetermined region. Further measurement parameters can be set in step 23, such as a slice thickness for example, a slice spacing, and a table speed at which the patient 4 is moved through the bore 5 of the tomography apparatus 2. The further measurement parameters can be chosen such that the resulting magnetic resonance images have a satisfactory image quality for a further planning of the magnetic resonance and positron emission tomography session.

In step 24, magnetic resonance data are acquired using the optimized readout gradient field with continuously advancing table. As described hereintofore, the readout gradient field is optimized for a specific region outside of the normally usable field of view and a specific slice position. When the patient 4 on the continuously advancing table 3 is continuously moved through the tomography apparatus 2, the anatomical structure of the patient 4 can also be acquired with low distortion or free of distortion in the region outside of the normally usable field of view. Corresponding magnetic resonance images are generated on the basis of said magnetic resonance data in step 25. Attenuation correction information for a positron emission tomography scan is then generated from the magnetic resonance images (step 26). The attenuation correction information takes into account in particular the anatomy of the patient both inside the normally usable field of view and in the optimized region outside of the normally usable field of view. The entire magnetic resonance/positron emission tomography session is furthermore planned on the basis of the generated magnetic resonance images (step 27), i.e. the magnetic resonance images are used in a similar way to images of a localizer sequence for planning the ensuing actual examination. Since only a low resolution of the magnetic resonance images is necessary for generating the planning information and the attenuation correction information, the magnetic resonance data acquired in step 24 can be acquired at a lower resolution than that of the actual examination, with the result that the acquisition of the magnetic resonance data in step 24 can be completed in a relatively short period of time. In the next step 28, a magnetic resonance/positron emission tomography examination is performed on the basis of the planning carried out in step 27. The results of the positron emission tomography examination are corrected in step 29 using the previously determined attenuation correction information.

Since the magnetic resonance data acquired in step 24 are used both for generating the attenuation correction information (step 26) and for planning the magnetic resonance/positron emission tomography examination (step 27), the entire method for performing an MR/PET examination can be completed in a much shorter time than in the case of an examination in which the attenuation correction information is acquired in an additional step, for example within the scope of an additional acquisition of magnetic resonance images or in the course of a method in which missing portions of the attenuation correction map are estimated retrospectively from the PET data by way of a maximum-likelihood a-posteriori algorithm for example.

The acquisition of MR data using the optimized readout gradient field (step 24) can also be performed for example using a mixed spin echo/gradient echo sequence or using a multi-echo sequence. In this case a plurality of different readout gradient fields can be used in order to enable MR data to be acquired with low distortion or free of distortion at a plurality of different optimized locations outside of the normally usable field of view.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing a combined magnetic resonance/positron emission tomography scan of an examination object in a magnetic resonance/positron emission tomography (MR/PET) system, the method comprising:
   acquiring first magnetic resonance data using a first readout gradient field such that, at a location of a field of view of a magnetic resonance system of the MR/PET system, a distortion caused by a nonlinearity of the first readout gradient field and a distortion caused by a $B_0$ field inhomogeneity reduce the effect of each other;
   generating first magnetic resonance images on the basis of the first magnetic resonance data;
   determining an attenuation correction map for a positron emission tomography scan on the basis of the first magnetic resonance images;
   acquiring positron emission data based on the first magnetic resonance images and second magnetic resonance data based on the first magnetic resonance images, the acquiring acquires the second magnetic resonance data using a second readout gradient field; and
   correcting the positron emission data using the attenuation correction map.

2. The method of claim 1, wherein the second readout gradient field is independent of the first readout gradient field.

3. The method of claim 1, wherein the first magnetic resonance data are acquired at a first resolution and the second magnetic resonance data are acquired at a second resolution, the second resolution being relatively higher than the first resolution.

4. The method of claim 1, wherein the acquisition of the first magnetic resonance data includes a continuous moving of the examination object through the MR/PET system.

5. The method of claim 1, wherein the location, at which the distortion caused by the nonlinearity of the first readout gradient field and the distortion caused by the $B_0$ field inhomogeneity reduce the effect of each other, includes a location in a peripheral region of the field of view.

6. The method of claim 5, wherein the MR/PET system includes a tunnel-shaped bore for receiving the examination object, the peripheral region of the field of view including an inner casing area along an inner surface of the tunnel-shaped bore.

7. The method of claim 6, wherein the inner casing area has an inner casing thickness of approximately 5 cm.

8. The method of claim 1, wherein the first magnetic resonance data are acquired in a transverse plane in relation to the examination object.

9. The method of claim 1, wherein the acquiring the first magnetic resonance data comprises:
   determining the first readout gradient field such that, at the location of the field of view, the distortion caused by the nonlinearity of the first readout gradient field and the distortion caused by the $B_0$ field inhomogeneity reduce the effect of each other,
   determining a further readout gradient field such that at a further location of the field of view, that is different from the location, a distortion caused by a nonlinearity of the further readout gradient field and the distortion caused by the $B_0$ field inhomogeneity reduce the effect of each other, and
   performing a multi-echo sequence, wherein following a 180° pulse, magnetic resonance data of a first spin echo are acquired using the first readout gradient field and following a further 180° pulse, further magnetic resonance data of a second spin echo are acquired using the further readout gradient field, wherein the first magnetic resonance images are determined on the basis of the magnetic resonance data of the first spin echo and the further magnetic resonance data.

10. The method of claim 1, wherein the acquiring the first magnetic resonance data comprises:
   determining the first readout gradient field such that, at the location of the field of view, the distortion caused by the nonlinearity of the first readout gradient field and the distortion caused by the $B_0$ field inhomogeneity reduce the effect of each other, the location of the field of view being a first location, determining a further readout gradient field in such a way that, at a second location of the field of view that is different from the first location, a distortion caused by a nonlinearity of the further readout gradient field and the distortion caused by the $B_0$ field inhomogeneity reduce the effect of each other, and performing a mixed spin echo/gradient echo sequence, wherein following a 180° pulse of the spin echo sequence, magnetic resonance data of a first spin echo are acquired using the first readout gradient field and subsequently further magnetic resonance data are acquired using the further readout gradient field, wherein the first magnetic resonance images are determined on the basis of the magnetic resonance data of the first spin echo and the further magnetic resonance data.

11. A non-transitory computer-readable medium configured to cause a control device to perform the method of claim 1 when executed by the control device, the control device being part of the MR/PET system.

* * * * *